United States Patent
Baumann et al.

(10) Patent No.: US 9,939,701 B2
(45) Date of Patent: Apr. 10, 2018

(54) PROTIC-SOLUBLE ORGANIC ELECTROCHROMIC COMPOUNDS

(71) Applicant: Gentex Corporation, Zeeland, MI (US)

(72) Inventors: Kelvin L. Baumann, Holland, MI (US); Rongguang Lin, Holland, MI (US); Punam Giri, Holland, MI (US); Sue Franz, Zeeland, MI (US)

(73) Assignee: GENTEX CORPORATION, Zeeland, MI (US)

( * ) Notice: Subject to any disclaimer, the term of this patent is extended or adjusted under 35 U.S.C. 154(b) by 0 days.

(21) Appl. No.: 15/065,808

(22) Filed: Mar. 9, 2016

(65) Prior Publication Data

US 2017/0146880 A1    May 25, 2017

Related U.S. Application Data

(60) Provisional application No. 62/257,950, filed on Nov. 20, 2015, provisional application No. 62/258,051, filed on Nov. 20, 2015.

(51) Int. Cl.
| | | |
|---|---|---|
| *C07D 213/22* | (2006.01) | |
| *G02F 1/15* | (2006.01) | |
| *C07D 241/46* | (2006.01) | |
| *C07D 213/04* | (2006.01) | |

(52) U.S. Cl.
CPC ............ *G02F 1/15* (2013.01); *C07D 213/04* (2013.01); *C07D 213/22* (2013.01); *C07D 241/46* (2013.01); *G02F 2001/1512* (2013.01); *G02F 2001/1515* (2013.01)

(58) Field of Classification Search
None
See application file for complete search history.

(56) References Cited

U.S. PATENT DOCUMENTS

| | | |
|---|---|---|
| 4,297,401 A | 10/1981 | Chern et al. |
| 4,418,102 A | 11/1983 | Ferrato |
| 4,695,490 A | 9/1987 | McClelland et al. |
| 4,902,108 A | 2/1990 | Byker |
| 5,140,455 A | 8/1992 | Varaprasad et al. |
| 5,294,376 A | 3/1994 | Byker |
| 5,596,023 A | 1/1997 | Tsubota et al. |
| 5,596,024 A | 1/1997 | Horie et al. |
| 5,770,114 A | 6/1998 | Byker et al. |
| 5,818,625 A | 10/1998 | Forgette et al. |
| 5,888,431 A | 3/1999 | Tonar et al. |
| 5,940,201 A | 8/1999 | Ash et al. |
| 5,998,617 A | 12/1999 | Srinivasa et al. |
| 6,020,987 A | 2/2000 | Baumann et al. |
| 6,057,956 A | 5/2000 | Ash et al. |
| 6,137,620 A | 10/2000 | Guarr et al. |
| 6,157,480 A | 12/2000 | Anderson et al. |
| 6,188,505 B1 | 2/2001 | Lomprey et al. |
| 6,193,912 B1 | 2/2001 | Thieste et al. |
| 6,249,369 B1 | 6/2001 | Theiste et al. |
| 6,268,950 B1 | 7/2001 | Ash et al. |
| 6,597,489 B1 | 7/2003 | Guarr et al. |
| 6,635,194 B2 | 10/2003 | Kloeppner et al. |
| 6,700,692 B2 | 3/2004 | Tonar et al. |
| 6,710,906 B2 | 3/2004 | Guarr et al. |
| 6,714,334 B2 | 3/2004 | Tonar |
| 7,256,925 B2 * | 8/2007 | Noh ........................ G02F 1/155 359/265 |
| 7,372,609 B2 | 5/2008 | Lin et al. |
| 7,372,611 B2 | 5/2008 | Tonar et al. |
| 7,428,091 B2 | 9/2008 | Baumann et al. |
| 7,830,583 B2 | 11/2010 | Neuman et al. |
| 8,228,590 B2 | 7/2012 | Baumann et al. |
| 8,323,534 B2 | 12/2012 | Percec et al. |
| 8,368,992 B2 | 2/2013 | Neuman et al. |
| 8,559,093 B2 | 10/2013 | Varaprasad et al. |
| 8,599,467 B2 | 12/2013 | Agrawal et al. |
| 8,928,966 B1 | 1/2015 | Kloeppner et al. |
| 2002/0015214 A1 | 2/2002 | Nishikitani et al. |
| 2002/0048678 A1 | 4/2002 | Hunia et al. |
| 2002/0141032 A1 | 10/2002 | Guarr et al. |
| 2002/0171081 A1 | 11/2002 | Vincent et al. |
| 2003/0039020 A1 | 2/2003 | Lomprey et al. |
| 2005/0162728 A1 | 7/2005 | Warner et al. |
| 2000/0077511 | 4/2006 | Hunia et al. |

(Continued)

FOREIGN PATENT DOCUMENTS

| | | |
|---|---|---|
| JP | 5181438 B2 * | 4/2013 |
| WO | WO-98/42796 A1 | 10/1998 |

(Continued)

OTHER PUBLICATIONS

Hakii et al, Chemical Abstracts 148:225761 (2008) corresponds to JP 5181438.*
Hakii et al, English Translation of JP 5181438 Apr. (Year: 2013).*
International Search Report and Written Opinion received in PCT/US2016/021619, dated Jun. 20, 2016 (32 pages).
International Search Report and Written Opinion received in PCT/US2016/021621, dated Jul. 6, 2016 (18 pages).
International Search Report and Written Opinion received in PCT/US2016/021630, dated Jan. 3, 2017 (22 pages).

(Continued)

*Primary Examiner* — Zinna Northington Davis
(74) *Attorney, Agent, or Firm* — Foley & Lardner LLP; Bradley D. Johnson

(57) ABSTRACT

Protic-soluble electrochromic materials, ion-paired electrochromic materials including protic-soluble electrochromic materials, as well as electrochromic media and electrochromic devices incorporating such materials, are provided. The use of protic solvent mixtures, especially mixtures incorporating water, allows for the use of a wider variety of substrate materials. For example, plastics that may be soluble in organic aprotic solvent systems may be used in water-based devices.

10 Claims, 1 Drawing Sheet

(56) References Cited

U.S. PATENT DOCUMENTS

| | | |
|---|---|---|
| 2007/0206263 A1 | 9/2007 | Neuman et al. |
| 2008/0310007 A1 | 12/2008 | Agrawal et al. |
| 2011/0003070 A1 | 1/2011 | Pozo Gonzalo et al. |
| 2011/0147680 A1 | 6/2011 | Percec et al. |
| 2012/0032104 A1 | 2/2012 | Amb et al. |
| 2013/0235323 A1 | 9/2013 | Sotzing et al. |

FOREIGN PATENT DOCUMENTS

| | | |
|---|---|---|
| WO | WO-99/02621 | 1/1999 |
| WO | WO-2014/025348 A1 | 2/2014 |

OTHER PUBLICATIONS

Yang, Y. H. et al. Macromol, 2011, 44, 1450-1459.
U.S. Office Action on U.S. Appl. No. 15/065,788, dated Feb. 27, 2017 (11 pages).
U.S. Office Action on U.S. Appl. No. 15/065,788, dated Mar. 21, 2017 (6 pages).
Vollhardt, K.P.C., et al., Organic Chemistry: Structure and Function, 1999, 3rd Ed., Freeman and Company, New York, New York, NY.
U.S. Office Action on U.S. Appl. No. 15/065,730, dated Nov. 7, 2017 (11 pages).

\* cited by examiner

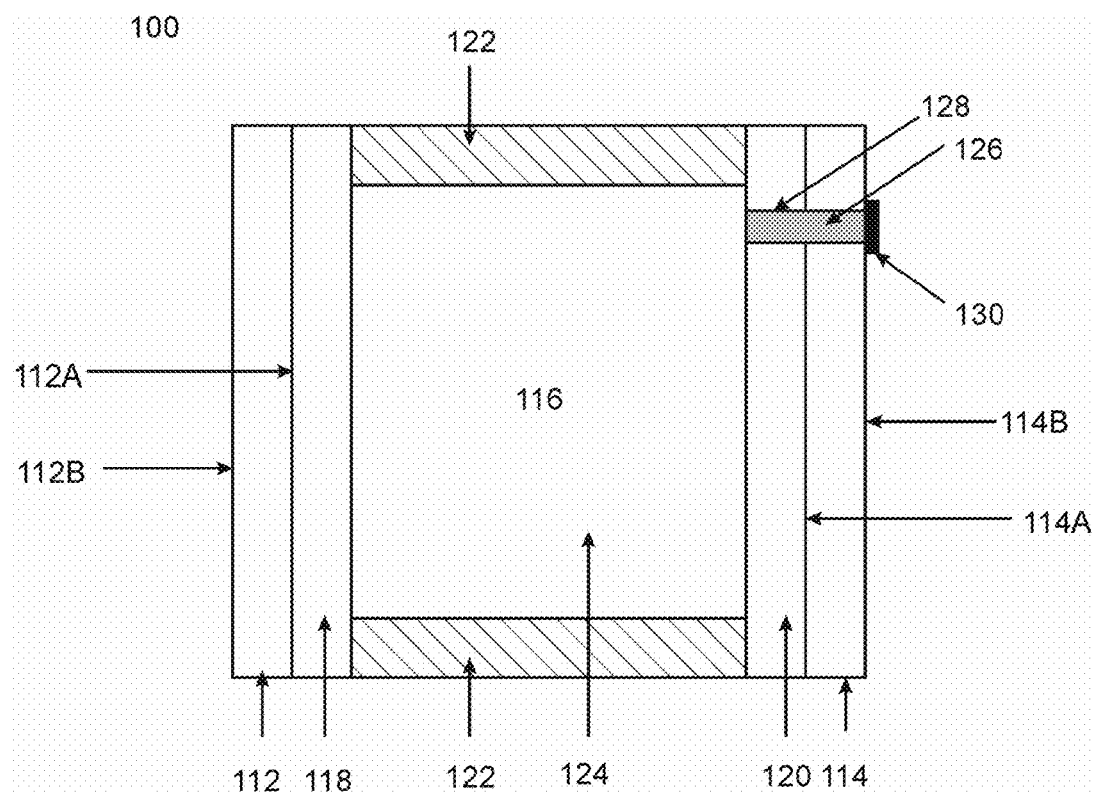

PROTIC-SOLUBLE ORGANIC ELECTROCHROMIC COMPOUNDS

CROSS-REFERENCE TO RELATED APPLICATIONS

This application claims the benefit of U.S. Provisional Patent Application No. 62/257,950, filed on Nov. 20, 2015, and U.S. Provisional Patent Application No. 62/258,051, filed on Nov. 20, 2015, the entire disclosures of which are incorporated herein by reference for any and all purposes.

FIELD

The present technology is generally related to electrochromic compounds and devices that employ such compounds. More particularly, it is related to protic soluble electrochromic compounds and electrochromic devices which incorporate them.

SUMMARY

In one aspect, protic-soluble electrochromic materials are provided. Further provided is an electrochromic medium that includes a cathodic material, an anodic material, and a liquid or gel that includes a protic solvent, where at least one of the cathodic or anodic materials is a protic-soluble electrochromic material as described herein.

In a related aspect, ion-paired electrochromic materials are provided that are useful in electrochromic devices. In some embodiments, the ion-paired electrochromic material includes a cathodic compound with a positive net charge (a "net positive cathodic compound") and an anodic compound with a negative net charge (a "net negative anodic compound"); in some embodiments, the ion-paired electrochromic material includes a net negative cathodic compound and a net positive anodic compound. In all embodiments, the charges on the anodic electrochromic compound and the charges on the cathodic electrochromic compound cancel out such that the ion-paired electrochromic material does not include a non-electrochromic counter-ion. In all embodiments, the net charge of the ion-paired electrochromic material is zero. Further provided is an electrochromic medium is provided that includes any embodiment of the ion-paired electrochromic material described herein and a liquid or gel. The liquid or gel includes a protic solvent.

In an aspect, an electrochromic device is provided which includes an electrochromic medium of any aspect or embodiment described herein, and at least one chamber defined by a first conductive surface of first substrate, a second conductive surface of a second substrate, and a sealing member joining the first substrate to the second substrate. The first and second substrates may be off-set to one another to allow for electric contact to be made with the first and second conductive surfaces.

BRIEF DESCRIPTION OF THE DRAWINGS

FIG. 1 is a cross-sectional schematic representation of an electrochromic device, according to one embodiment.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be constructed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, $C_m$-$C_n$, such as $C_1$-$C_{12}$, $C_1$-$C_8$, or $C_1$-$C_6$ when used before a group refers to that group containing m to n carbon atoms.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a perhaloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6- disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH=$CH_2$, C=$CH_2$, or C=CHCH$_3$.

As used herein, "aryl", or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

The term "carboxylate" as used herein refers to a —COO$^-$ group.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

The term "substantially transparent" as used herein will be understood by persons of ordinary skill in the art and will vary to some extent depending upon the context in which it is used. If there are uses of the term which are not clear to persons of ordinary skill in the art, given the context in which it is used, the term means that the material allows a light transmission of about 75% or more of a beam of light having a wavelength of 400 nm directed to the material at a specular angle of 10° through a thickness of 2 mm of the material.

In one aspect, electrochromic materials soluble in protic solvents ("protic-soluble electrochromic materials") are provided, where such materials may further be water-soluble. It is well appreciated that water is a type of protic solvent. "Protic-soluble" as used herein means at least 0.1 g of the material dissolves in 100 g of a protic solvent; "water-soluble" as used herein means at least 0.1 g of the material dissolves in 100 g of H$_2$O. The use of protic solvent mixtures, especially mixtures incorporating water, allows for the use of a wider variety of substrate materials. Such protic-soluble electrochromic materials include cathodic protic-soluble electrochromic materials, anodic protic-soluble electrochromic materials, or a combination thereof.

Cathodic protic-soluble electrochromic materials include a viologen represented by Formula (I):

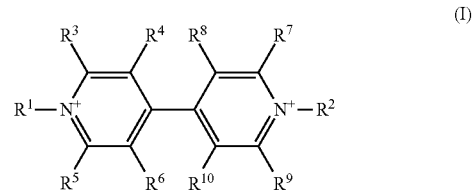

wherein $R^1$ and $R^2$ are each independently an alkyl group substituted with a carboxylate, phosphonate, phosphate, or sulfonate; and $R^3$, $R^4$, $R^5$, $R^6$, $R^7$, $R^8$, $R^9$, and $R^{10}$ are each independently H, OH, O-alkyl, F, Cl, Br, I, CN, NO$_2$, alkyl, or aryl. In any embodiment herein, $R^1$ and $R^2$ may each independently be —(CH$_2$)$_m$—CO$_2^-$, —(CH$_2$)$_n$—P(O)(OH)(O$^-$), —(CH$_2$)$_p$—OP(O)(OH)(O$^-$), or —(CH$_2$)$_q$—OS(O)$_2$O$^-$, where m, n, p, and q are each independently 1, 2, 3, 4, 5, 6, 7, 8, 9, or 10. Representative cathodic protic-soluble electrochromic materials of Formula (I) include

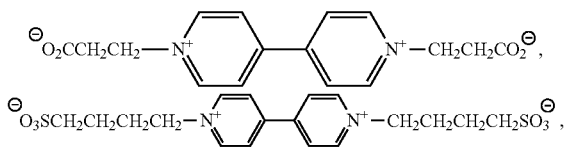

or mixtures thereof.

Cathodic protic-soluble electrochromic materials also include a viologen represented by Formula (II):

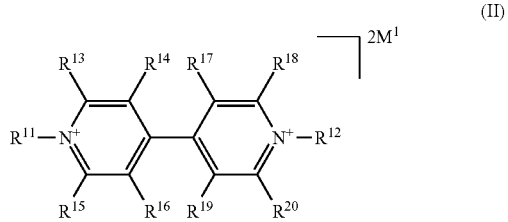

wherein $R^{11}$ and $R^{12}$ are each independently an alkyl group substituted with a N$^+$(R$^{21}$)$_3$ or P$^+$(R$^{22}$)$_3$; $R^{13}$, $R^{14}$, $R^{15}$, $R^{16}$, $R^{17}$, $R^{18}$, $R^{19}$, and $R^{20}$ are each independently H, OH, O-alkyl, F, Cl, Br, I, CN, NO$_2$, alkyl, or aryl; $R^{21}$ and $R^{22}$ are independently at each occurrence alkyl substituted with a carboxylate, phosphonate, phosphate, or sulfonate or phenyl substituted with a carboxylate, phosphonate, phosphate, or sulfonate; and M$^1$ is independently at each occurrence an alkali metal, an alkali earth metal, or an ammonium compounds. Representative ammonium compounds include $NH_4^+$, alkyl ammonium (e.g., $CH_3CH_2NH_3^+$), aralkyl ammonium (e.g., $PhCH_2NH_3^+$) dialkyl ammonium (e.g., $(CH_3CH_2)_2NH_2^+$), diaralkyl ammonium, alkyl aryl ammonium, alkyl aralkyl ammonium (e.g., $(PhCH_2)(CH_3CH_2)NH_2^+$)), trialkyl ammonium, triaralkyl ammonium, alkyl diaryl ammonium, dialkyl aryl ammonium, tetraalkyl ammonium (e.g., $(CH_3CH_2)_4N^+$), tetraaralkyl ammonium, alkyl triaralkyl ammonium, dialkyl diaralkyl ammonium, and trialkyl aralkyl ammonium (e.g., $(CH_3)_3(PhCH_2)N^+$). In any embodiment herein, $M^1$ may be $Li^+$, $Na^+$, or $K^+$. In any embodiment herein, $R^{21}$ and $R^{22}$ may independently at each occurrence be $-(CH_2)_s-CO_2^-$, $-Ph-CO_2^-$, $-(CH_2)_t-P(O)(OH)(O^-)$, $-Ph-P(O)(OH)(O^-)$, $-(CH_2)_u-OP(O)(OH)(O^-)$, $-Ph-OP(O)(OH)(O^-)$, $-(CH_2)_w-S(O)_2O^-$, or $-Ph-S(O)_2O^-$, where s, t, u, and w are each independently 1, 2, 3, 4, 5, 6, 7, 8, 9, or 10. The phenylene group ("-Ph-") of $R^{21}$ and $R^{22}$ may be a 1,2-phenylene, a 1,3-phenylene, or a 1,4-phenylene. A representative cathodic protic-soluble electrochromic material of Formula (II) is

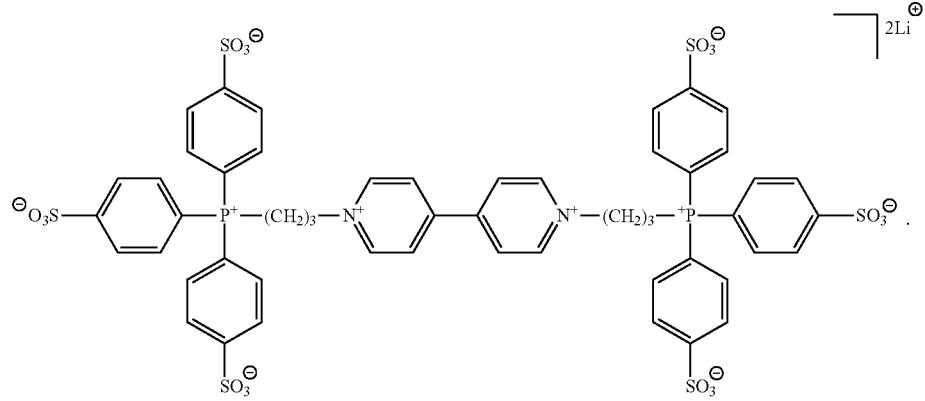

Anodic protic-soluble electrochromic materials include those represented by Formula (III):

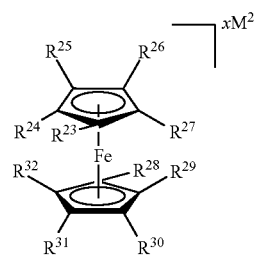

(III)

where $R^{23}$ and $R^{28}$ are each independently alkyl or alkyl substituted with a carboxylate, phosphonate, phosphate, or sulfonate, provided that at least one is alkyl substituted with a carboxylate, phosphonate, phosphate, or sulfonate; $R^{24}$, $R^{25}$, $R^{26}$, $R^{27}$, $R^{29}$, $R^{30}$, $R^{31}$, and $R^{32}$ are each independently H or alkyl; x is an integer corresponding to the number of carboxylate, phosphonate, phosphate, sulfonate groups; and $M^2$ is independently at each occurrence be an alkali metal, an alkali earth metal, or an ammonium compound. In any embodiment herein, $M^2$ may independently at each occurrence be $Li^+$, $K^+$, or $Na^+$. In any embodiment herein, $R^{23}$ and $R^{28}$ may each independently be alkyl, $-(CH_2)_{m'}-CO_2^-$, $-(CH_2)_{n'}-P(O)(OH)(O^-)$, $-(CH_2)_{p'}-OP(O)(OH)(O^-)$, or $-(CH_2)_{q'}-S(O)_2O^-$; where m', n', p', and q' are each independently 1, 2, 3, 4, 5, 6, 7, 8, 9, or 10. Representative anodic electrochromic compounds of Formula (III) include

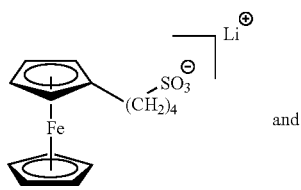 and

-continued

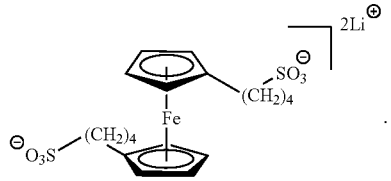

Anodic protic-soluble electrochromic materials include those represented by Formulas (IV), (V), and (VI)

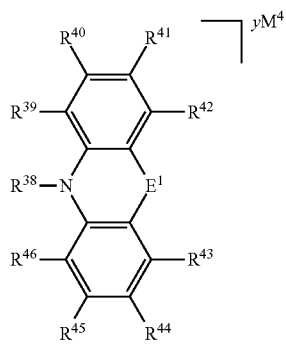

(IV)

-continued

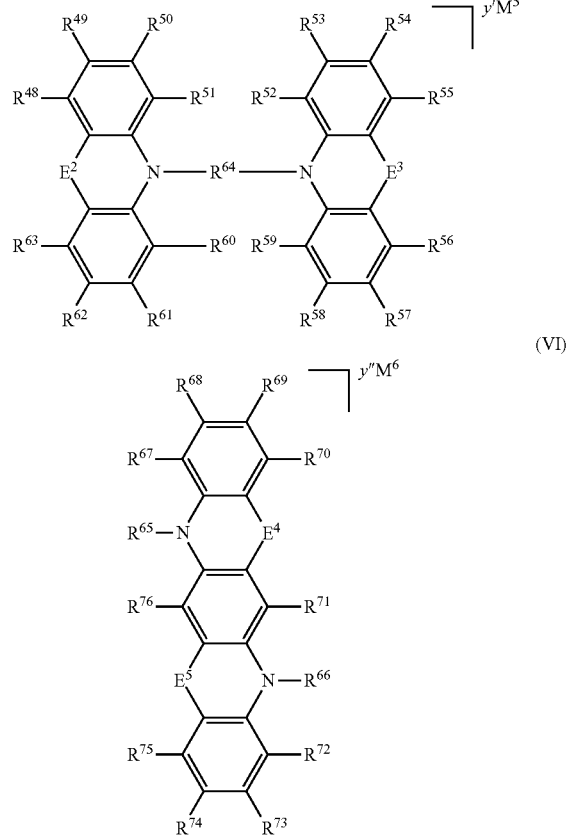

(V)

(VI)

where $E^1$, $E^2$, $E^3$, $E^4$, and $E^5$ are each independently O, S, or $NR^{47}$; $R^{38}$, $R^{47}$, $R^{65}$, and $R^{66}$ are independently at each occurrence an alkyl group substituted with a carboxylate, phosphonate, phosphate, or sulfonate; $R^{39}$, $R^{40}$, $R^{41}$, $R^{42}$, $R^{43}$, $R^{44}$, $R^{45}$, and $R^{46}$ are each independently H, F, Cl, Br, I, CN, OH, O-alkyl, SH, S-alkyl, $NO_2$, alkyl, aryl, or amino, or any two adjacent groups of $R^{39}$, $R^{40}$, $R^{41}$, $R^{42}$, $R^{43}$, $R^{44}$, $R^{45}$, and $R^{46}$ join to form a monocyclic, polycyclic, or heterocyclic group;
$R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ are each independently H, F, Cl, Br, I, CN, OH, O-alkyl, SH, S-alkyl, $NO_2$, alkyl, aryl, or amino, or any two adjacent groups of $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, and $R^{63}$ join to form a monocyclic, polycyclic, or heterocyclic group; and $R^{64}$ is an alkylene group;
$R^{67}$, $R^{68}$, $R^{69}$, $R^{70}$, $R^{71}$, $R^{72}$, $R^{73}$, $R^{74}$, $R^{75}$, and $R^{76}$ are each independently H, F, Cl, Br, I, CN, OH, O-alkyl, SH, S-alkyl, $NO_2$, alkyl, aryl, or amino, or any two adjacent groups of $R^{67}$, $R^{68}$, $R^{69}$, $R^{70}$, $R^{72}$, $R^{73}$, $R^{74}$, and $R^{75}$ join to form a monocyclic, polycyclic, or heterocyclic group;
y, y', and y'' are each independently an integer corresponding to the number of carboxylate, phosphonate, phosphate, sulfonate groups; and
$M^4$, $M^5$, and $M^6$ are independently at each occurrence an alkali metal, an alkali earth metal, or an ammonium compound. In any embodiment herein, $M^4$, $M^5$, and $M^6$ may independently at each occurrence be $Li^+$, $Na^+$, or $K^+$.

In any embodiment herein, $R^{38}$, $R^{47}$, $R^{65}$, and $R^{66}$ may independently at each occurrence be $-(CH_2)_m-CO_2^-$, $-(CH_2)_n-P(O)(OH)(O^-)$, $-(CH_2)_p-OP(O)(OH)(O^-)$, or $-(CH_2)_q-S(O)_2O^-$; where m, n, p, and q are each independently 1, 2, 3, 4, 5, 6, 7, 8, 9, or 10.

As an example, anodic protic-soluble electrochromic materials of Formula (IV) include, but are not limited to,

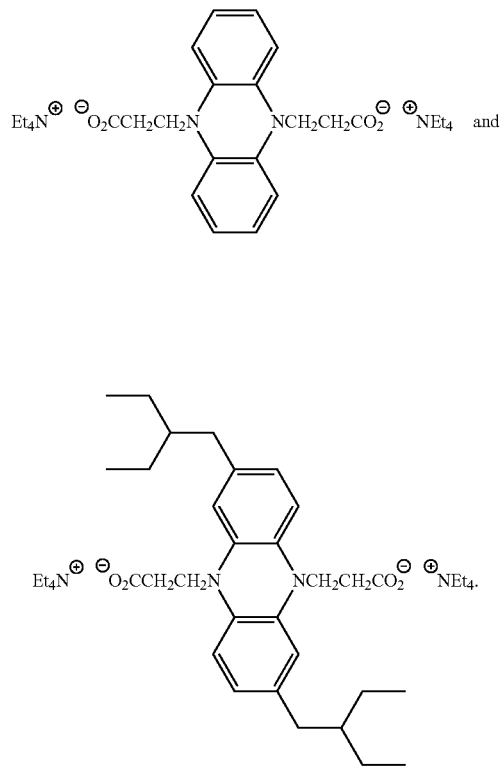

In an aspect, ion-paired electrochromic materials are provided that are useful in electrochromic devices. "Ion-paired electrochromic materials" as described herein are compounds that include at least one anodic electrochromic compound and at least one cathodic electrochromic compound, where the net charge of the anodic electrochromic compound(s) and the net charge of the cathodic electrochromic compound(s) cancel out such that the ion-paired electrochromic material does not include a non-electrochromic counter-ion. The ion-paired electrochromic materials provide devices that have lower current for a similar light transmission change in comparison to devices that include combination of anodic and cathodic electrochromic compounds that are not ion-paired.

In some embodiments, the ion-paired electrochromic material includes at least one cathodic compound with a positive net charge (a "net positive cathodic material") and at least one anodic material with a negative net charge (a "net negative anodic compound"). In such embodiments, the ion-paired electrochromic material may include one or more net positive cathodic electrochromic compounds of Formula (VII), (VIII), or (IX) and one or more net negative anodic compounds of Formula (IVa), (Va), (VIa), or (Ma), where the net charge of the ion-paired electrochromic material is zero.

Cathodic electrochromic compounds of Formula (VII), (VIII), or (IX) are represented by the following structural formulas:

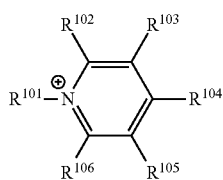

(VII)

where $R^{101}$ is alkyl group; and $R^{102}$, $R^{103}$, $R^{104}$, $R^{105}$, and $R^{106}$ are each independently H, OH, O-alkyl, F, Cl, Br, I, CN, SCN, OCN, $NO_2$, alkyl, or aryl;

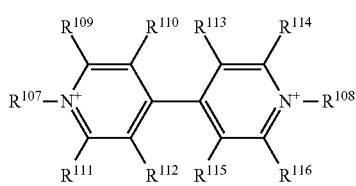

(VIII)

where $R^{107}$ and $R^{108}$ are each independently alkyl or an alkyl group substituted with a trialkyl ammonium, a triphenyl ammonium, a trialkyl phosphinium, or a triphenyl phosphinium; $R^{109}$, $R^{110}$, $R^{111}$, $R^{112}$, $R^{113}$, $R^{114}$, $R^{115}$, and $R^{116}$ are each independently H, OH, O-alkyl, F, Cl, Br, I, CN, $NO_2$, alkyl, or aryl; and

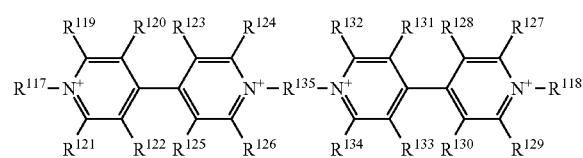

(IX)

where $R^{117}$ and $R^{118}$ are each independently alkyl or an alkyl group substituted with a trialkyl ammonium, a triphenyl ammonium, a trialkyl phosphinium, or a triphenyl phosphinium; $R^{119}$, $R^{120}$, $R^{121}$, $R^{122}$, $R^{123}$, $R^{124}$, $R^{125}$, $R^{126}$, $R^{127}$, $R^{128}$, $R^{129}$, $R^{130}$, $R^{131}$, $R^{132}$, $R^{133}$, and $R^{134}$ are each independently H, OH, F, Cl, Br, I, CN, $NO_2$, alkyl, or aryl; $R^{135}$ is $(CH_2)_a$, arylene, or aralkylene; and a is an integer from 1 to 12.

By way of example, representative cathodic electrochromic compounds of Formula (VIII) include, but are not limited to,

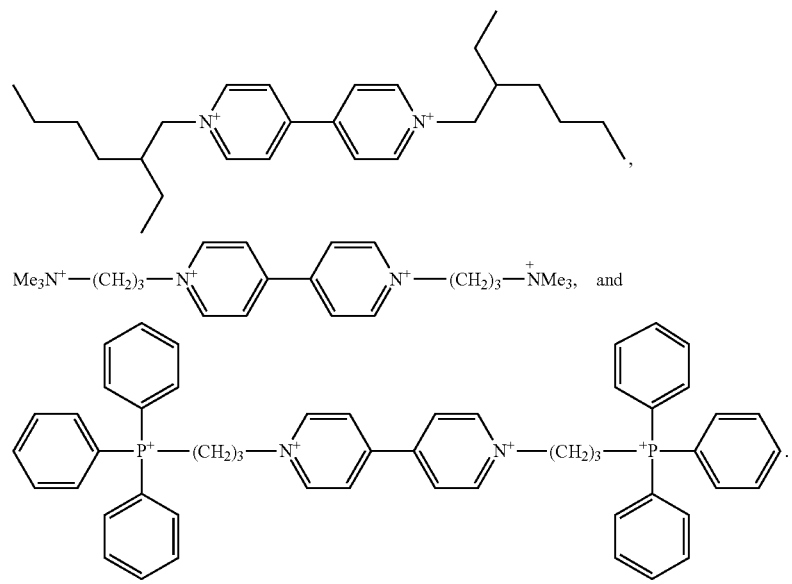

Prior to being included in the ion-paired electrochromic material, cathodic electrochromic compounds of Formula (VII), (VIII), or (IX) may include an appropriate number of anions to provide a neutral salt and may include a mixture of two or more anions. In any of the above embodiments and aspects, it may be that any anion is a halide, a borate, a fluoroborate, a tetraaryl borate, a hexafluoro metal or metalloid, a sulfate, a sulfonate, a sulfonamide, a carboxylate, a perchlorate, a tetrachloroferrate, or (when two or more anions are present) a mixture of any two or more anions thereof. In any of the above embodiments and aspects, the anion may be $F^-$, $Cl^-$, $Br^-$, $I^-$, $BF_4^-$, $PF_6^-$, $SbF_6^-$, $AsF_6^-$, $ClO_4^-$, $N(CF_3SO_2)_2^-$, $C(CF_3SO_2)_3^-$, triflate, $N(SO_2C_2F_5)$—, or $BAr_4^-$, wherein Ar is an aryl, fluorinated aryl, or a bis(trifluoromethyl)aryl group.

Anodic electrochromic compounds of Formula (IVa), (Va), or (VIa) are represented by the following structural formulas:

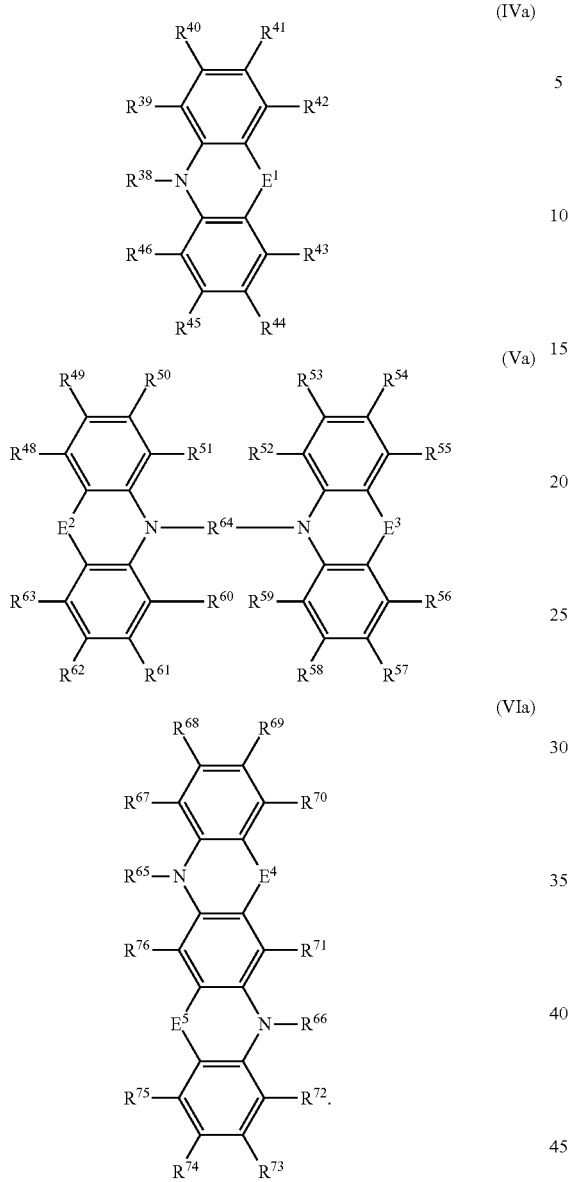
Notably, these are the anodic protic-soluble electrochromic compounds of Formulas (IV), (V), and (VI) where $M^4$, $M^5$, and $M^6$ have been exchanged with the one or more net positive cathodic electrochromic compounds of the ion-paired electrochromic material.
Representative anodic electrochromic compounds of Formula (IVa) or (VIa) include, but are not limited to,
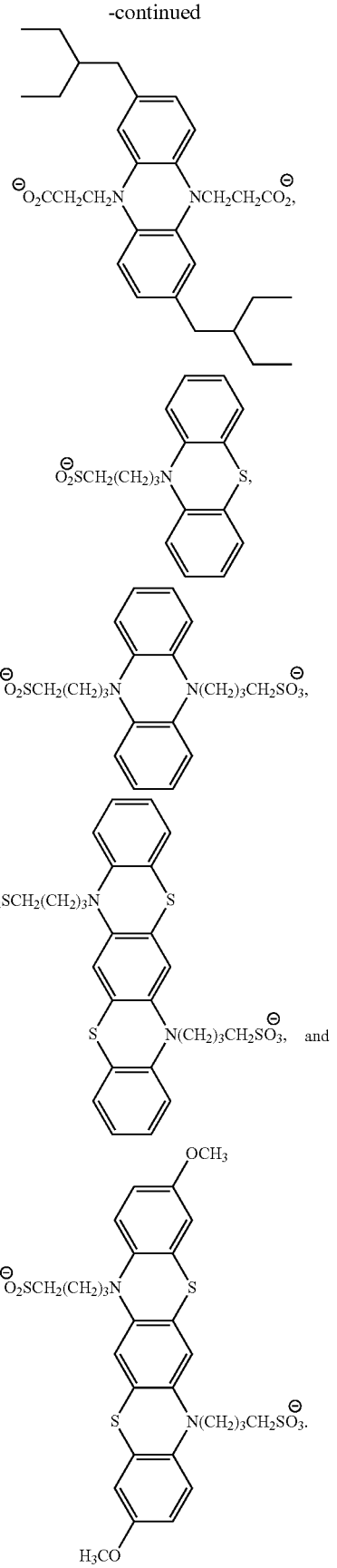

Anodic electrochromic compounds of Formula (Ma) are represented by the following structural formula:

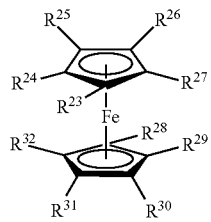
(IIIa)

Notably, these are the anodic protic-soluble electrochromic compounds of Formula (III), where $M^2$ has been exchanged with the one or more net positive cathodic electrochromic compounds of the ion-paired electrochromic material. Representative anodic electrochromic compounds of Formula (Ma) include

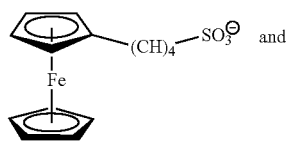 and

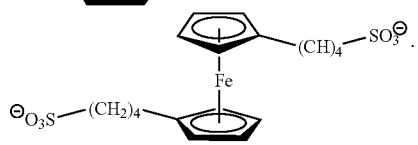

Such ion-paired electrochromic materials may include an equal number of net positive cathodic electrochromic compounds and net negative anodic electrochromic compounds where the net positive cathodic electrochromic compound has an equal (but opposite) net charge as the net negative anodic electrochromic compound. Ion-paired electrochromic materials may also include an unequal number of net positive cathodic electrochromic compounds and net negative anodic electrochromic compounds where the net positive cathodic electrochromic compound has an different (but opposite) net charge in comparison with the net negative anodic electrochromic compound. Representative ion-paired electrochromic materials that include at least one net positive cathodic compound and at least one net negative anodic compound include, but are not limited to,

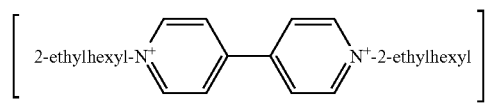

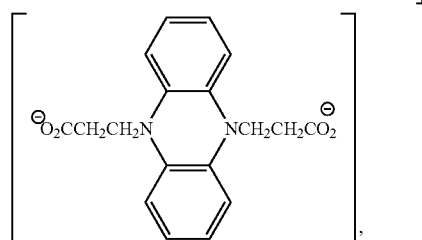

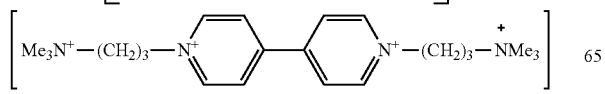

-continued

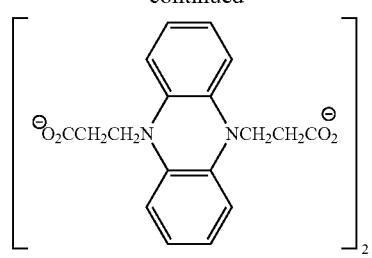

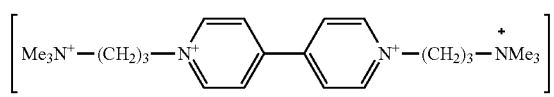

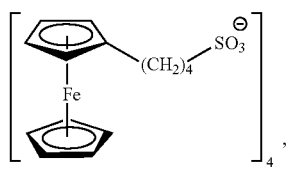

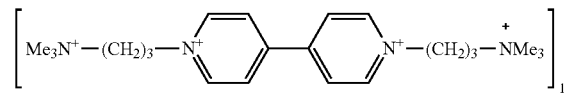

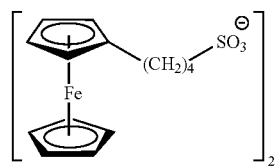

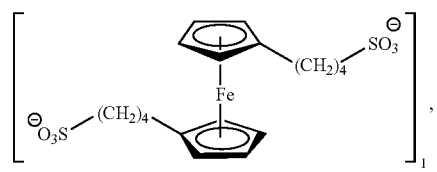

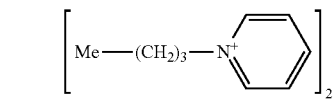

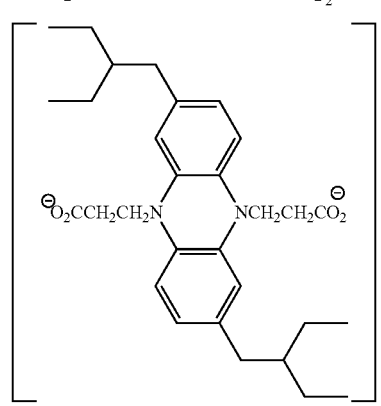

-continued

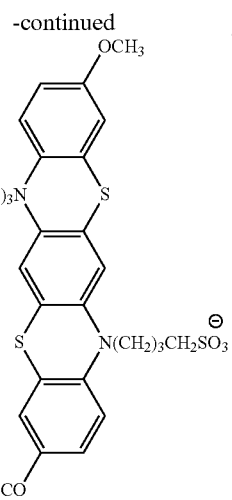

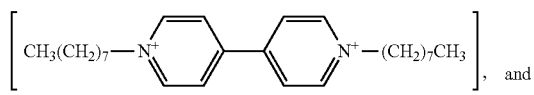, and

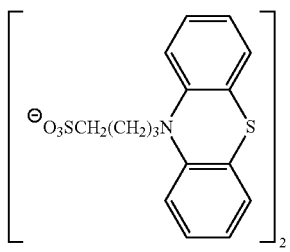

-continued

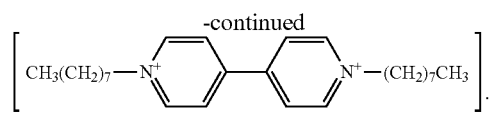

In some embodiments, the ion-paired electrochromic material includes at least one cathodic compound with a negative net charge (a "net negative cathodic electrochromic compound") and at least one anodic electrochromic compound with a positive net charge (a "net positive anodic electrochromic compound"). In such embodiments, the ion-paired electrochromic material may include one or more net negative cathodic electrochromic compounds of Formula (IIa) and one or more net positive anodic electrochromic compounds of Formula (X), (XI), (XII), or (XIII), where the net charge of the ion-paired electrochromic material is zero.

Net negative cathodic electrochromic compounds of Formula (IIa) are represented by the following structural formula:

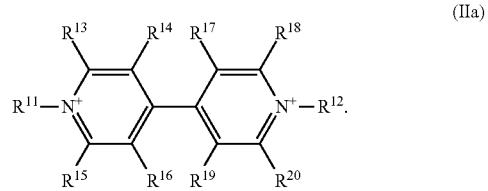

These are the cathodic protic-soluble electrochromic compounds of Formula (IIa), where $M^1$ has been exchanged with the one or more net positive anodic electrochromic compounds of the ion-paired electrochromic material. A representative net negative cathodic electrochromic compound of Formula (IIa) is

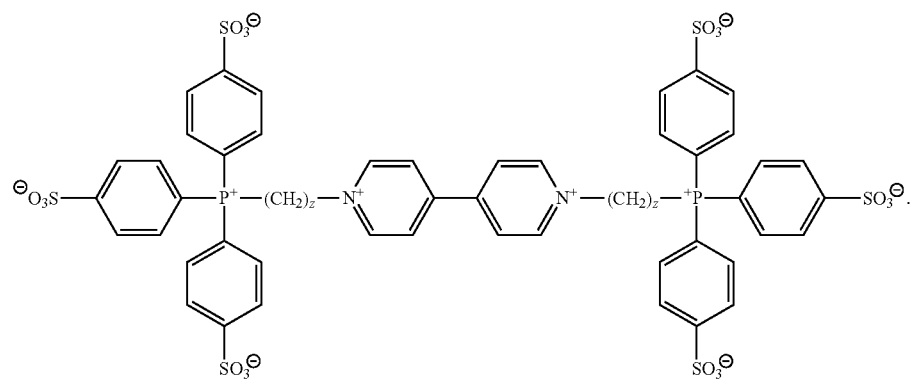

This net negative cathodic electrochromic compound includes four positive charges (two from the pyridinium groups and two from the phosphinium groups) and six negative charges so that the compound has a net charge that is negative 2.

Net positive anodic electrochromic compounds of Formula (X), (XI), or (XII) are represented by the following structural formulas:

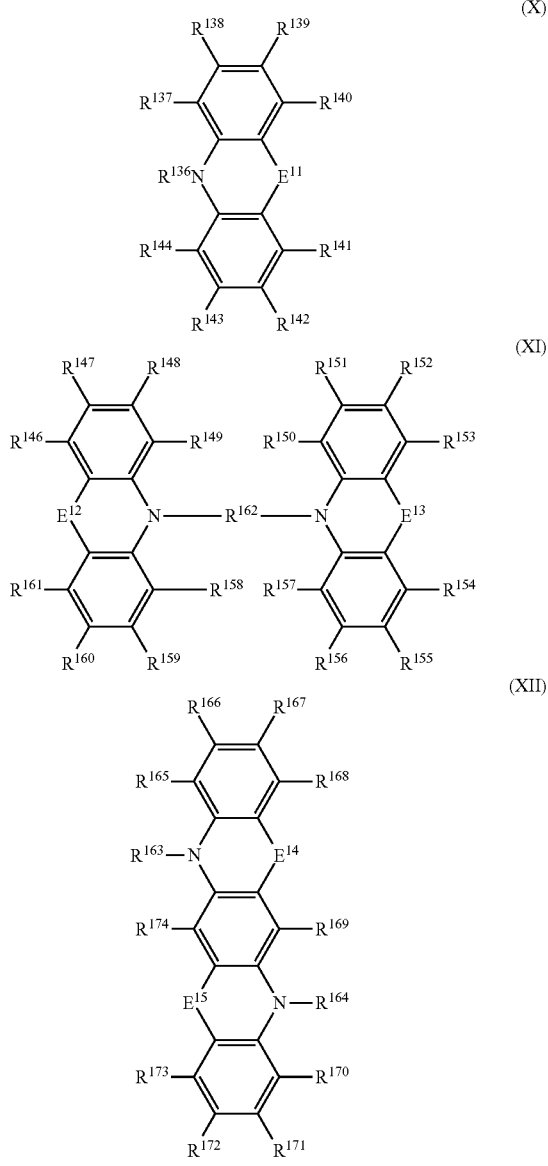

where $E^{11}$, $E^{12}$, $E^{13}$, $E^{14}$, and $E^{15}$ are each independently O, S, or $NR^{145}$;

$R^{136}$, $R^{145}$, $R^{163}$, and $R^{164}$ are independently at each occurrence an alkyl substituted with a trialkyl ammonium, a triphenyl ammonium, a trialkyl phosphinium, or a triphenyl phosphinium;

$R^{137}$, $R^{138}$, $R^{139}$, $R^{140}$, $R^{141}$, $R^{142}$, $R^{143}$, and $R^{144}$ are each independently H, F, Cl, Br, I, CN, OH, O-alkyl, SH, S-alkyl, $NO_2$, alkyl, aryl, or amino, or any two adjacent groups of $R^{137}$, $R^{138}$, $R^{139}$, $R^{140}$, $R^{141}$, $R^{142}$, $R^{143}$, and $R^{144}$ join to form a monocyclic, polycyclic, or heterocyclic group;

$R^{146}$, $R^{147}$, $R^{148}$, $R^{149}$, $R^{150}$, $R^{151}$, $R^{152}$, $R^{153}$, $R^{154}$, $R^{155}$, $R^{156}$, $R^{157}$, $R^{158}$, $R^{159}$, $R^{160}$, and $R^{161}$ are each independently H, F, Cl, Br, I, CN, OH, O-alkyl, SH, S-alkyl, $NO_2$, alkyl, aryl, or amino, or any two adjacent groups of $R^{146}$, $R^{147}$, $R^{148}$, $R^{149}$, $R^{150}$, $R^{151}$, $R^{152}$, $R^{153}$, $R^{154}$, $R^{155}$, $R^{156}$, $R^{157}$, $R^{158}$, $R^{159}$, $R^{160}$, and $R^{161}$ join to form a monocyclic, polycyclic, or heterocyclic group; and $R^{62}$ is an alkylene group; and $R^{165}$, $R^{166}$, $R^{167}$, $R^{168}$, $R^{169}$, $R^{170}$, $R^{171}$, $R^{172}$, $R^{173}$, and $R^{174}$ are each independently H, F, Cl, Br, I, CN, OH, O-alkyl, SH, S-alkyl, $NO_2$, alkyl, aryl, or amino, or any two adjacent groups of $R^{165}$, $R^{166}$, $R^{167}$, $R^{168}$, $R^{70}$, $R^{171}$, $R^{172}$, and $R^{173}$ join to form a monocyclic, polycyclic, or heterocyclic group.

Representative net positive anodic electrochromic compounds of Formula (X) or (XII) include, but are not limited to,

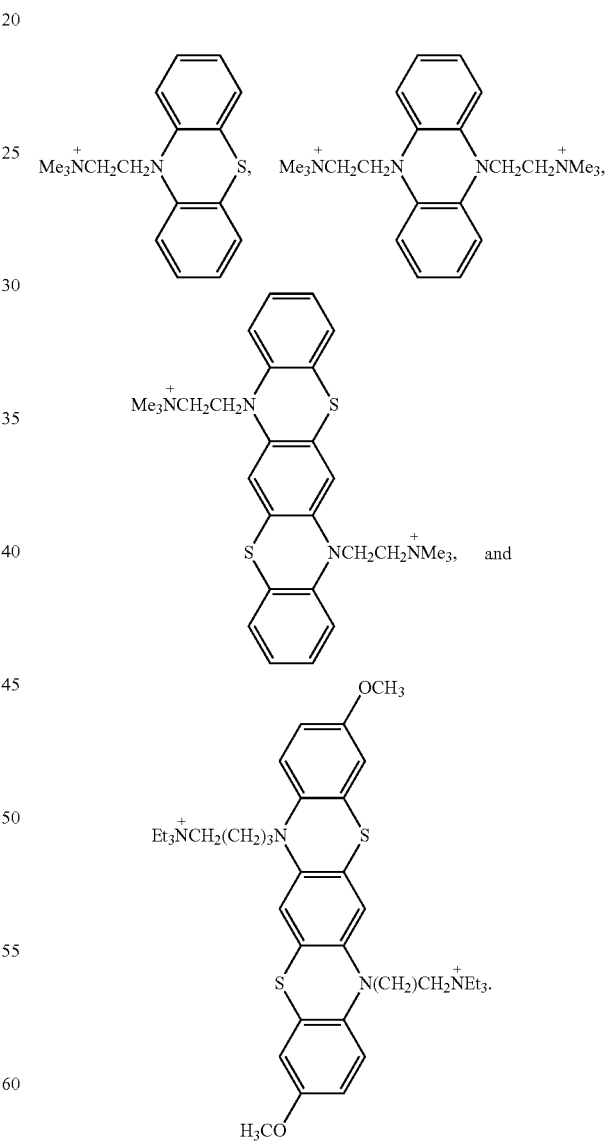

Net positive anodic electrochromic compounds of Formula (XIII) are represented by the following structural formula:

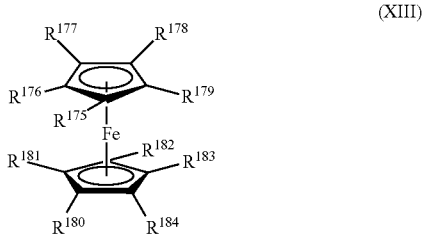

(XIII)

where $R^{175}$ and $R^{180}$ are each independently alkyl or alkyl substituted with a trialkyl ammonium, a triphenyl ammo-

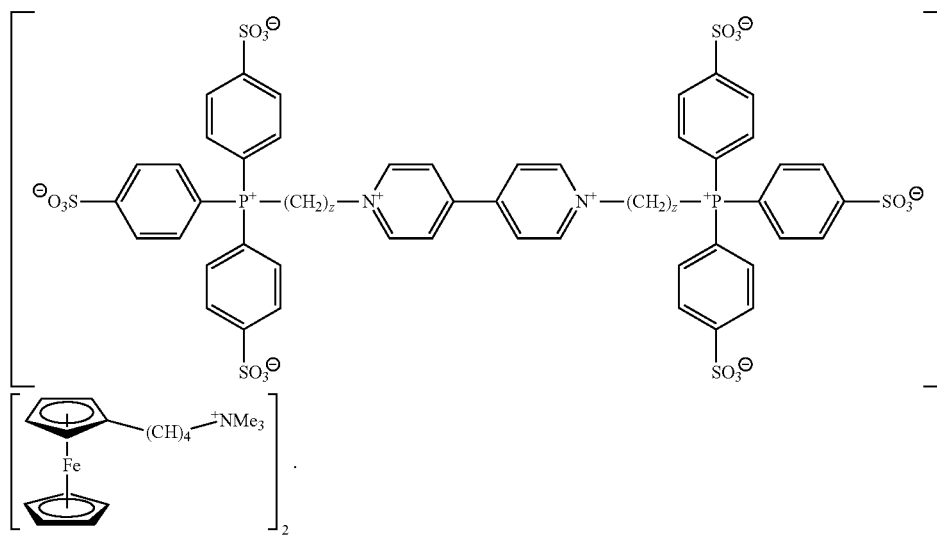

nium, a trialkyl phosphinium, or a triphenyl phosphinium provided that at least one is alkyl substituted with a trialkyl ammonium, a triphenyl ammonium, a trialkyl phosphinium, or a triphenyl phosphinium; and $R^{176}$, $R^{177}$, $R^{178}$, $R^{179}$, $R^{181}$, $R^{182}$, $R^{183}$, and $R^{184}$ are each independently H or alkyl. Representative net positive anodic electrochromic compounds of Formula (XIII) include, but are not limited to,

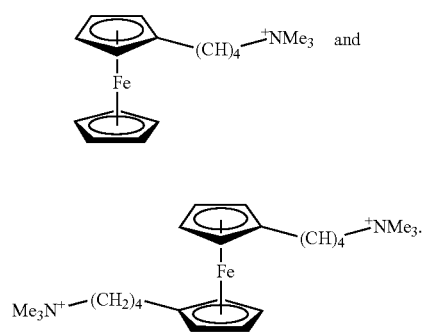

Prior to being included in the ion-paired electrochromic material, net positive anodic electrochromic compounds of Formula (X), (XI), (XII), or (XIII), may include an appropriate number of anions to provide a neutral salt and may include a mixture of two or more anions. In any of the above embodiments and aspects, it may be that any anion is a halide, a borate, a fluoroborate, a tetraaryl borate, a hexafluoro metal or metalloid, a sulfate, a sulfonate, a sulfonamide, a carboxylate, a perchlorate, a tetrachloroferrate, or (when two or more anions are present) a mixture of any two or more anions thereof. In any of the above embodiments and aspects, the anion may be $F^-$, $Cl^-$, $Br^-$, $I^-$, $BF_4^-$, $PF_6^-$, $SbF_6^-$, $AsF_6^-$, $ClO_4^-$, $N(CF_3SO_2)_2^-$, $C(CF_3SO_2)_3^-$, triflate, $N(SO_2C_2F_5)^-$, or $BAr_4^-$, wherein Ar is an aryl, fluorinated aryl, or a bis(trifluoromethyl)aryl group.

Representative ion-paired electrochromic materials that include a net negative cathodic electrochromic compound and a net positive anodic electrochromic compound include, but are not limited to, In another aspect, an electrochromic medium is provided that includes a cathodic material, an anodic material, and a liquid or gel that includes a protic solvent, where at least one of the cathodic or anodic materials is a protic-soluble electrochromic material of any aspect or embodiment described herein, or the electrochromic medium includes an ion-paired electrochromic material of any aspect or embodiment herein and a liquid or gel that includes a protic solvent.

Typically, both of the anodic and cathodic materials are electroactive. It will be understood that regardless of its ordinary meaning, the term "electroactive" will be defined herein as a material that undergoes a modification in its oxidation state upon exposure to a particular electrical potential difference. Additionally, it will be understood that the term "electrochromic" will be defined herein, regardless of its ordinary meaning, as a material that exhibits a change in its extinction coefficient at one or more wavelengths upon exposure to a particular electrical potential difference.

The cathodic material may include one or more viologens. For example, the cathodic material may include one or more embodiments of the cathodic protic-soluble electrochromic materials of Formulas (I) and (II) and neutral salts of compounds of Formulas (VII), (VIII), (IX). Cathodic electrochromic materials include, but are not limited to, those as described in U.S. Pat. Nos. 4,902,108; 5,998,617; and 6,193,912.

The cathodic material may further include a polymer film, such as various substituted polythiophenes, polymeric viologens, an inorganic film, or a solid transition metal oxide, including, but not limited to, tungsten oxide.

The anodic material may include any one or more embodiments of the anodic protic-soluble electrochromic material of Formulas (III)-(VI) and neutral salts of compounds of Formulas (X), (XI), (XII), and (XIII). Illustrative anodic materials may include, but are not limited to, metallocenes (including ferrocene, substituted ferrocenes, substituted ferrocenyl salts), 5,10-dihydrophenazines, phenazines, substituted phenazines, phenothiazines, substituted phenothiazines (including substituted dithiazines), thianthrene, substituted thianthrenes phenoxadines, phenoxazines, carbazoles, hydrazones, triphenodithiazones, triphenoxazines, triphendioxazines, and related substituted or unsubstituted compounds. Examples of anodic materials may include 5,10-dimethyl-5,10-dihydrophenazine (DMP), 3,7,10-trimethylphenothiazine, 2,3,7,8-tetramethoxy-thianthrene, 10-methylphenothiazine, tetramethylphenazine (TMP), bis(butyltriethylammonium)-para-methoxytriphenodithiazine (TPDT), and 3,10-dimethoxy-7,14-(triethylammoniumbutyl)-triphenodithiazinebis(tetrafluoroborate).

It is also contemplated that the anodic material may include a polymer film, such as polyaniline, polythiophenes, polymeric metallocenes, or a solid transition metal oxide, including, but not limited to, oxides of vanadium, nickel, iridium, as well as numerous heterocyclic compounds, etc. It will be understood that numerous other anodic materials are contemplated for use including those disclosed in U.S. Pat. Nos. 4,902,108; 6,188,505; 6,710,906; and 7,428,091.

The liquid or gel includes a protic solvent. Protic solvents as used herein include, but are not limited to, alcohols (e.g., methanol ($CH_3OH$), ethanol (EtOH), isopropanol (iPrOH), trifluoroethanol (TFE), butanol (BuOH), ethylene glycol, propylene glycol), carboxylic acids (e.g., formic acid, acetic acid, propanoic acid, butanoic acid, pentanoic acid, lauric acid, stearic acid, deoxycholic acid, glutamic acid, glucuronic acid), ammonia ($NH_3$), a primary amino compound (e.g., methyl amine, ethyl amine, propyl amine), a secondary amino compound (e.g., dimethyl amine, diethyl amine, di(n-propyl) amine), water, or a mixture of any two or more thereof. Thus, in any of the above embodiments and aspects, the protic solvent may include an alcohol, a carboxylic acid, a primary amino compound, a secondary amino compound, water, or a mixture of any two or more thereof. In any embodiments described herein, the protic solvent may include a diol. In any embodiment described herein, the protic solvent may include water. The amount of protic solvent in the liquid or gel may be about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 99 wt %, about 100 wt %, or any range including or in between any two of these values. The amount of water in the liquid or gel may be about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 99 wt %, about 100 wt %, or any range including or in between any two of these values.

The liquid or gel may also include an aprotic solvent. An aprotic solvent as used herein includes, but is not limited to, a carbonate, a halogenated solvent, an ether, an ester, a ketone, a tertiary amide, a nitrile, a sulfoxide, a sulfone, or a mixture of any two or more thereof. In any of the above embodiments and aspects, the aprotic solvent may be a polar aprotic solvent. Polar aprotic solvents as used herein include, but are not limited to, ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), carbonates (e.g., ethylene carbonate, propylene carbonate, trimethylene carbonate), amides (e.g., dimethylformamide (DMF), dimethylacetamide (DMA)), nitriles (e.g., acetonitrile ($CH_3CN$), propionitrile ($CH_3CH_2CN$), benzonitrile (PhCN)), sulfoxides (e.g., dimethyl sulfoxide), sulfones (e.g., sulfolane), ionic liquids (such as pyridinium-, imidazolium-, and pyrrolidinium-compounds), or a mixture of any two or more thereof. Where the solvent includes an ionic liquid, the counterion of the ionic liquid may be $F^-$, $Br^-$, $I^-$, $BF_4^-$, $PF_6^-$, $SbF_6^-$, $AsF_6^-$, $ClO_4^-$, $SO_3CF_3^-$, $N(CN)_2^-$, $N(CF_3SO_2)_2^-$, $C(CF_3SO_2)_3^-$, $N(SO_2C_2F_5)^-$, $^-Al(OC(CF_3)_3)_4$ or $^-BAr_4$, wherein Ar is a aryl or fluorinated aryl group (such as a pentafluorophenyl group), or other counterions used in ionic liquids. In any of the above embodiments and aspects, the aprotic solvent may include a cyclic carbonate such as ethylene carbonate, propylene carbonate, butylene carbonate, trimethylene carbonate, 2,2-dimethyltrimethylene carbonate, a cyclic ester such as α-acetolactone, β-propiolactone, γ-butyrolactone, γ-valerolactone, δ-valerolactone, γ-caprolactone, δ-caprolactone, ε-caprolactone, or a combination of any two or more thereof. In any of the above embodiments and aspects, the amount of aprotic solvent in the liquid or gel may be about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, or any range including or in between any two of these values.

While specific solvents have been disclosed, numerous other solvents that would be known to those having ordinary skill in the art having the present disclosure before them are likewise contemplated for use. For example, in addition to the solvent, the electrochromic medium may be a gel composition.

In the electrochromic medium, one or more materials may undergo a change in phase during the operation of the device, for example a material contained in solution in the ionically conducting electrolyte forms a layer on the electrically conducting electrode when electrochemically oxidized or reduced.

In addition, the electrochromic medium may include other materials, such as light absorbers, light stabilizers, thermal stabilizers, antioxidants, thickeners, viscosity modifiers, tint providing agents, redox buffers, and mixtures of any two or more such materials. Illustrative UV-stabilizers may include, but are not limited to, 2-ethyl-2-cyano-3,3-diphenyl acrylate; (2-ethylhexyl)-2-cyano-3,3-diphenyl acrylate; 2-(2'-hydroxy-4'-methylphenyl)benzotriazole, sold by Ciba-Geigy Corp. under the trademark Tinuvin P; 3-[3-(2H-benzotriazole-2-yl)-5-(1,1-dimethylethyl)-4-hydroxyphenyl]propionic acid pentyl ester prepared from Tinuvin 213, sold by Ciba-Geigy Corp., via conventional hydrolysis followed by conventional esterification (hereinafter "Tinuvin PE"); 2,4-dihydroxybenzophenone; 2-hydroxy-4-methoxybenzophenone; and 2-ethyl-2'-ethoxyalanilide. Exemplary UV stabilizers include those represented by Formula (XIV):

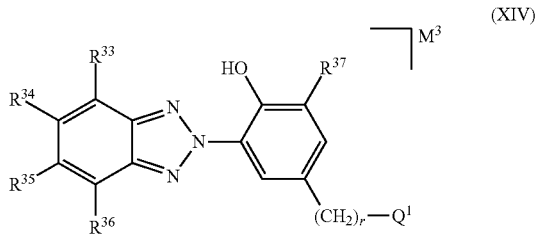

where $R^{33}$, $R^{34}$, $R^{35}$, and $R^{36}$ are each independently H, OH, O-alkyl, F, Cl, Br, I, CN, $NO_2$, alkyl, or aryl; $R^{37}$ is alkyl or aryl; $Q^1$ is a carboxylate, a phosphonate, a phosphate, or a sulfonate; $M^3$ is an alkali metal, an alkali earth metal, or an ammonium compound; and r is 1, 2, 3, 4, 5, 6, 7, 8, 9, or 10. $Q^1$ may be $CO_2^+$, $P(O)(OH)(O^-)$, $OP(O)(OH)(O^-)$, or $S(O)_2 O^-$. In any embodiment herein, $M^3$ may be $Li^+$, $Na^+$, or $K^+$.

The electrochromic medium may further include an anodic and/or cathodic color-stabilizing redox buffer. Suitable redox buffers include, among others, those disclosed in U.S. Pat. No. 6,188,505. Other examples of suitable anodic and cathodic redox buffers include, but are not limited to, metallocene (e.g., substituted ferrocenes), and metallocinium (e.g. ferrocinium) compounds.

The electrochromic medium may further include a cross-linked polymer matrix, a free-standing gel, a substantially non-weeping gel, and/or a thermoplastic.

The electrochromic medium may be made up in layers and includes a material attached directly to an electrically conducting electrode or confined in close proximity thereto which remains attached or confined when electrochemically oxidized or reduced.

In an aspect, electrochemical devices are provided incorporating an electrochromic medium of any aspect and embodiment described herein. The electrochemical device includes such an electrochromic medium, where the electrochromic medium includes a cathodic material, an anodic material, and a liquid or gel that includes a protic solvent.

In a related aspect, an electrochromic device is provided which includes an electrochromic medium of any aspect and embodiment described herein, and at least one chamber defined by a first conductive surface of first substrate, a second conductive surface of a second substrate, and a sealing member joining the first substrate to the second substrate. The electrochromic medium is disposed within the chamber and may be according to any of the previously described embodiments of an electrochromic medium. The first and second substrates may be off-set to one another to allow for electric contact to be made with the first and second conductive surfaces.

A schematic representation of an electrochromic device is shown in FIG. 1. The electrochromic device 100 includes first substrate 112 having a front surface 112A and a rear surface 112B, and a second substrate 114 having a front surface 114A and a rear surface 114B. The front surface 112A and the front surface 114A have associated therewith conductive surfaces 118 and 120, respectively. The first substrate 112 and the second substrate 114, along with a sealing member 122 define a chamber 116 for containing an electrochromic medium 124. The device also includes one or more plugs 126 and 130 associated with one or more fill ports 128. The one or more fill ports 128 may be disposed within the first substrate 112, the second substrate 114, or the sealing member 122. Upon mounting as a mirror, window, or other device, the electrochromic device 100 may optionally include a bezel that extends around a periphery of at least one of the first substrate 112 and the second substrate 114 to conceal and/or protect a bus connector (if present), the sealing member 122, one or more plugs 126 and 130, and the one or more fill ports 128.

Several other electrochromic device configurations are contemplated for use, including, but not limited to, those disclosed in U.S. Pat. Nos. 5,818,625; 6,597,489; and 6,700,692, all of which are hereby incorporated herein by reference in their entirety including all references incorporated therein.

The first substrate may be fabricated from any one of a number of materials that are transparent or substantially transparent in the visible region of the electromagnetic spectrum, such as, for example, borosilicate glass, soda lime glass, natural and synthetic polymeric resins, plastics, and/or composites including polyesters (e.g. PET), polyimides (PI), polycarbonates, polysulfones, polyethylene naphthalate (PEN), ethylene vinyl acetate (EVA), acrylate polymers, as well as Topas®. In another embodiment, the first substrate is fabricated from a sheet of glass having a thickness ranging from about 0.10 millimeters (mm) to about 12.7 mm. This may include any range of thickness such as from about 0.50 mm to about 1.50 mm, or from about 0.65 mm to about 1.00 mm. Of course, the thickness of the substrate will depend upon the particular application of the electrochromic device. While particular substrate materials have been disclosed, for illustrative purposes only, it will be understood that numerous other substrate materials are likewise contemplated for use so long as the materials are at least substantially transparent and exhibit appropriate physical properties, such as strength, to be able to operate effectively in conditions of intended use. Indeed, electrochromic devices in accordance with the present invention can be, during normal operation, exposed to extreme temperature variation as well as substantial UV radiation, emanating primarily from the sun. It will be further understood that first substrate and/or second substrate may comprise a UV absorbing layer and/or contain a UV absorbing material to help protect the substrate(s) and/or the electrochromic media from UV damage.

In some embodiments, the second substrate may be fabricated from similar materials as that of the first substrate, or where transparency of the second substrate is not desired, the second substrate may be a metal. The second substrate is fabricated from a sheet of glass or plastic having a thickness ranging from about 0.10 mm to about 12.7 mm. This may include thicknesses from about 0.50 mm to about 1.50 mm, or from about 0.65 mm to about 1.00 mm. If the first and second substrates are fabricated from sheets of glass, then the glass can optionally be tempered, heat strengthened, chemically strengthened, and/or laminated prior to or subsequent to being coated with layers of electrically conductive material.

One or more layers of electrically conductive material may be associated with the rear surface of the first substrate. These layers serve as an electrode for the electrochromic device. Electrically conductive material is desirably a material that: (a) is substantially transparent in the visible region of the electromagnetic spectrum; (b) bonds reasonably well to the first substrate; (c) maintains this bond when associated with a sealing member; (d) is generally resistant to corrosion from materials contained within the electrochromic device or the atmosphere; and (e) exhibits minimal diffuse or specular reflectance as well as sufficient electrical conductance. It is contemplated that the electrically conductive material may be fabricated from fluorine doped tin oxide (FTO), for example TEC glass, indium/tin oxide (ITO), doped zinc oxide, indium zinc oxide, metal oxide/metal/metal oxide (wherein metal oxide can be substituted with metal carbide, metal nitride, metal sulfide, etc.), or other materials known to those having ordinary skill in the art.

One or more layers of an electrically conductive material made of the same or different materials as those associated with the rear surface of the first substrate may be associated the front surface of the second substrate. The electrically conductive material may be operatively bonded to electrically conductive material associate with the first substrate by a sealing member. Once bonded, the sealing member, plug and/or the juxtaposed portions of electrically conductive materials may serve to generally define an inner peripheral geometry of a chamber. Alternatively, edge sealing techniques may be utilized which are disclosed in U.S. Pat. No. 7,372,611.

In some embodiments, the first substantially transparent substrate and second substantially transparent substrate have a cell distance of less than 600 µm. In another embodiment, the first substantially transparent substrate and second substantially transparent substrate have a cell distance of about 50 µm to about 600 µm, about 150 µm to about 600 µm, about 200 µm to about 300 µm, about 225 µm to about 275 µm, or ranges between any two of these values (including endpoints). In another embodiment, the first substantially transparent substrate and second substantially transparent substrate have a cell distance of about 350 µm, about 300 µm, about 275 µm, about 250 µm, about 225 µm, about 200 µm, about 175 µm, about 150 µm, about 125 µm, about 100 µm, about 75 µm, about 50 µm, or ranges between any two of these values (including endpoints). In another embodiment, the first substantially transparent substrate and second substantially transparent substrate have a cell distance of about 250 µm.

In some embodiments, the sealing member may include any material that is configured to adhesively bond to the electrically conductive materials coated on the first and second substrate to, in turn, seal a chamber, (in certain embodiments in cooperation with a plug and fill port so that electrochromic composition does not inadvertently leak out of the chamber. It is also contemplated that the sealing member extends all the way to rear surface and front surface of their respective substrates. In such an embodiment, the layers of electrically conductive material coated on the first and second substrates may be partially removed where the sealing member is positioned. If the electrically conductive materials are not associated with their respective substrates, then the sealing member preferably bonds well to glass. It will be understood that sealing member can be fabricated from any one of a number of materials including, for example, those disclosed in U.S. Pat. Nos. 4,297,401; 4,418,102; 4,695,490; 5,596,023; 5,596,024; 6,157,480; and 6,714,334.

In any embodiment or aspect herein, the concentration of the anodic and/or cathodic materials in the electrochromic medium may be from about 1 millimolar (mM) to about 500 mM. For example, the concentration of the anodic and/or cathodic materials in the electrochromic medium may be from about 1 mM to about 100 mM, where the concentration of each anodic and/or cathodic material may independently be about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 22 mM, about 24 mM, about 26 mM, about 28 mM, about 30 mM, about 32 mM, about 34 mM, about 36 mM, about 38 mM, about 40 mM, about 42 mM, about 44 mM, about 46 mM, about 48 mM, about 50 mM, about 55 mM, about 60 mM, about 65 mM, about 70 mM, about 75 mM, about 80 mM, about 85 mM, about 90 mM, about 95 mM, about 100 mM, or any range including and in between any two of these values.

Illustrative electrochromic devices employing protic-soluble electrochromic compounds as described herein may include, for illustrative purposes only, a window, an aircraft transparency, a mirror, a display device, and the like. It will be understood that like or analogous elements and/or components, and/or methods referred to herein, may be identified throughout the drawings with like reference characters. In some embodiments, the electrochromic device is an electrochromic window or an electrochromic mirror. In some embodiments, the device is a vehicular interior electrochromic mirror. In some embodiments, the device is a variable transmission electrochromic window. In some embodiments, the device is an aircraft window system. Other applications of the electrochromic device includes screens for watches, calculators and computer display screens; eye wear such as eyeglasses and sunglasses; switchable mirrors, sun visors; automobile, architectural, aircraft, marine, and spacecraft windows; information display boards and digital billboards and the like.

The electrochromic devices described herein advantageously employ protic solvent mixtures allowing for the use of a wider variety of substrate materials.

The electrochromic devices employing ion-paired electrochromic materials have lower current for a similar light transmission change in comparison to a combination of anodic and cathodic electrochromic materials that are not ion-paired.

The present invention, thus generally described, will be understood more readily by reference to the following examples, which are provided by way of illustration and are not intended to be limiting of the present invention.

EXAMPLES

The following examples more specifically illustrate protocols for preparing compounds and devices according to various embodiments described above. These examples should in no way be construed as limiting the scope of the present technology.

Example 1

To a 2 liter round bottom flask under nitrogen was charged 400 mL acetonitrile, phenazine (45.0 g; 250 mmol), sodium dithionite (52.2 g; 300 mmol), sodium carbonate monohydrate (62.0 g; 500 mmol), methyl 3-bromopropionate (167 g; 1,000 mmol), and tributylmethylammonium chloride (11.3 g; 37.5 mmol) and mixed at reflux. After 48 hours of mixing at reflux, $H_2O$ (40 mL; 18 MΩ-cm reverse osmosis deoionized) was added to the mixture over 1 hour. 72 hours following completion of the $H_2O$ addition, the mixture was vacuum filtered, washed with chilled ethanol, and recrystallized from an acetane/ethanol mixture to provide 1 as a white crystalline solid in 85% yield.

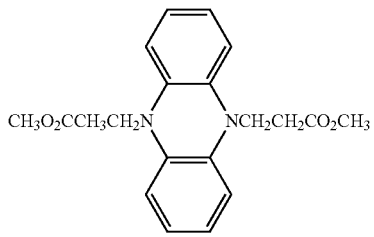

Example 2

Compound 1 dissolved in methanol to a concentration of 0.25 M, to which was added an 4 equivalents of tetraethyl ammonium hydroxide and the mixture allowed to reflux for 24 hours. Compound 2 was isolated from the mixture by distilling off the water and adding ethanol and acetone. After distillation of most of these solvents, the desired product crystallized and precipitated as a pure white solid.

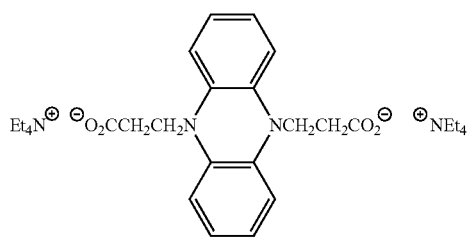

Example 3

Compound 1 (30 g) was dissolved in toluene (240 mL), and to this was added 2-ethyl butyric anhydride (68.5 g) followed by zinc chloride powder (5.4 g) and the mixture stirred and heated at 90° C. until completion of the reaction (about 3 hours). The mixture was washed with 1 N aqueous HCl (100 mL) for 5 minutes followed by removal of the toluene and addition of hexane to provide compound 3 as an oil. The supernatant containing unreacted 2-ethyl butyric anhydride was decanted off.

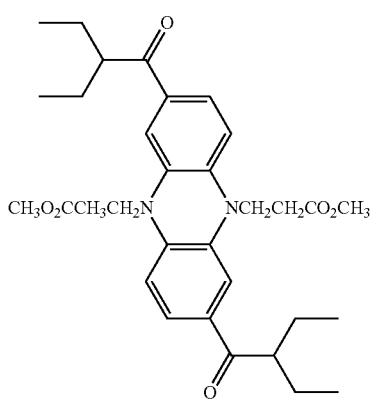

Compound 3 was dissolved in toluene (400 mL) and to this was slowly added $AlCl_3$ powder (11.4 g) and the mixture stirred at room temperature for about 0.5 hours. THF (100 mL) was then slowly added and borane dimethylsulfide (17 mL) was slowly added, whereupon the reaction allowed to proceed at room temperature for 2 hours. The mixture was then heated to 50° C. and the reaction allowed to proceed to completion. The reaction was quenched by slow additional of water, followed by addition of ethanol, and then dilute aqueous HCl (1 M). The water layer was then removed followed by concentration of the mixture to provide an oil. This oil was dissolved in hot methanol and cooled to crystallize compound 4 (23 g).

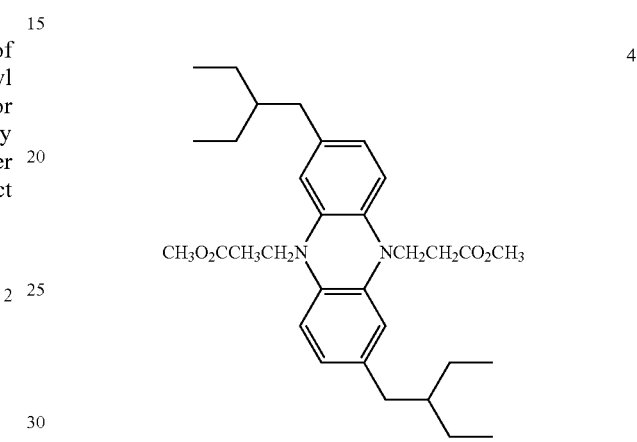

Compound 4 was dissolved in methanol (190 mL) and to this was added 2.5 M tetraethyl ammonium hydroxide (40 mL), whereupon the mixture was stirred at 50° C. overnight. The solvent was then removed followed by addition of ethanol (150 mL), water (75 mL), and acetone (100 mL) to allow for recrystallization of compound 5 (7.8 g, 98.8% purity).

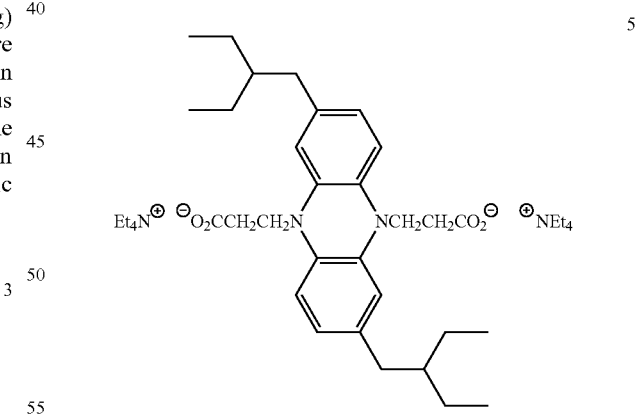

Example 4

To a 1 liter round bottom flask under argon was charged 4,4'-dipyridyl (15.6 g; 100 mmol), 3-bromopropionic acid (45.9 g; 300 mmol), sodium bicarbonate (33.6 g; 400 mmol), and 500 mL acetonitrile and the resulting mixture stirred for 72 hours at reflux, whereupon an additional 500 mL of acetonitrile was added. After 24 hours the mixture was filtered to yield a white solid which was washed with cold acetonitrile and then dissolved in $H_2O$ (18 MΩ-cm reverse osmosis deoionized). Ethanol was added to the solution to initiate precipitation of the product, whereupon recrystallization provided compound 6.

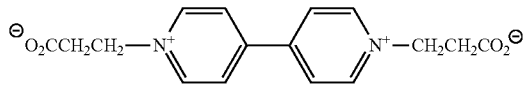

Example 5

To a 5 liter round bottom flask under nitrogen atmosphere was charged 4,4'-dipyridyl (156.0 g; 1.0 mol), 1,4-butane sultone (408.0 g; 3.0 mol), and 2 L acetonitrile, whereupon the mixture was stirred and heated to reflux. After 48 at reflux, the reaction mixture was cooled, filtered, and the solid washed with cold acetonitrile. The solid was then dissolved in $H_2O$ (18 MΩ-cm reverse osmosis deoionized) and recrystallized with ethanol. The resulting solid was then recrystallized in methanol to provide compound 7.

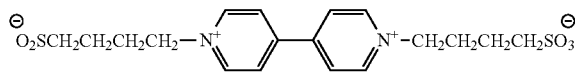

Example 6

To compound 1 (6.55 g) was added aqueous 1N NaOH (40 mL) and the mixture stirred at 80° C. until completion to provide the corresponding disodium biscarboxylate (compound 8). To this was added 2-ethylhexyl viologen dibromide (10.0 g) and the mixture stirred at 80° C. for 0.5 hours.

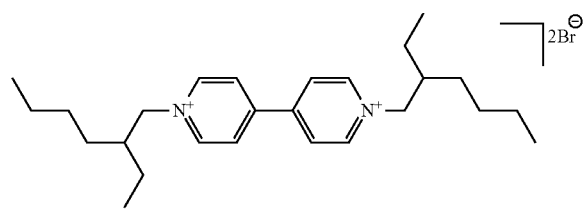

2-ethylhexyl viologen dibromide

The mixture was then neutralized with 1N HCl. The resulting ion-paired electrochromic compound 9 was initially isolated as a waxy solid. This waxy solid was recrystallized by dissolving in hot ethanol (200 mL) followed by removal of about 150 mL of the ethanol by distillation. Acetone (100 mL) was then added dropwise to precipitate a green crystalline compound, which was then dried under vacuum at room temperature to provide 4.3 grams of compound 9.

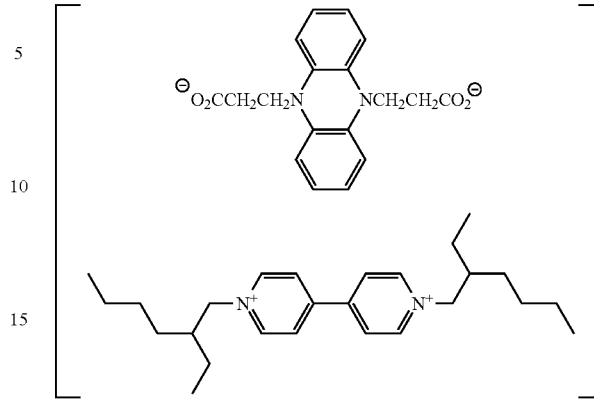

Example 7

An electrochromic device was prepared from two indium tin oxide (ITO) coated glass substrates, one of which was provided with two holes. The inward facing ITO-coated glass substrates were spaced apart by 130 micron spacers around the perimeter and sealed with a epoxy seal around the perimeter to form a chamber. A 25 mM solution of ion-paired salt 9 in propanediol was added to the chamber and the fill holes sealed. Upon application of 1.2 V the device colored from approximately 60% transmittance to 20% transmittance and exhibited a steady state current of 3 mA.

A comparative device was prepared with a propylene carbonate solution of 25 mM 5,10-dihydro, 5,10-dimethyl phenazine and 25 mM octyl viologen bis-tetrafluoroborate. Upon application of 1.2 V, the device darkened to 20% T with a steady state current of 33 mA.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. An electrochromic medium comprising a cathodic material, an anodic material, and a liquid or gel that comprises a protic solvent; wherein the electrochromic medium comprises at least one of
   a cathodic protic-soluble electrochromic material represented by Formula (I):

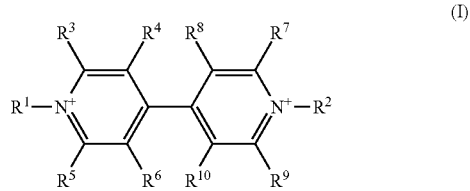

(I)

wherein
$R^1$ and $R^2$ are each independently —$(CH_2)_m$—$CO_2^-$, —$(CH_n)$—$P(O)(OH)(O^-)$, —$(CH_2)_p$—$OP(O)(OH)(O^-)$, or —$(CH_2)_q$—$S(O)_2O^-$;
$R^3$, $R^4$, $R^5$, $R^6$, $R^7$, $R^8$, $R^9$, and $R^{10}$ are each independently H, OH, O-alkyl, F, Cl, Br, I, CN, $NO_2$, alkyl, or aryl;

n is 2, 3, 4, 5, 6, 7, 8, 9, or 10;
m, p, and q are each independently 1, 2, 3, 4, 5, 6, 7, 8, 9, or 10;
a cathodic protic-soluble electrochromic material represented by Formula (II):

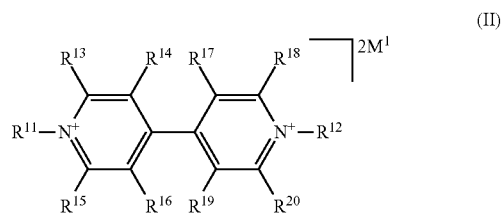

(II)

wherein
$R^{11}$ and $R^{12}$ are each independently an alkyl group substituted with a $N^+(R^{21})_3$ or $P^+(R^{22})_3$;
$R^{13}$, $R^{14}$, $R^{15}$, $R^{16}$, $R^{17}$, $R^{18}$, $R^{19}$, and $R^{20}$ are each independently H, OH, O-alkyl, F, Cl, Br, I, CN, $NO_2$, alkyl, or aryl;
$R^{21}$ and $R^{22}$ are independently at each occurrence be alkyl substituted with a carboxylate, phosphonate, phosphate, or sulfonate or phenyl substituted with a carboxylate, phosphonate, phosphate, or sulfonate; and
$M^1$ is independently at each occurrence an alkali metal, an alkali earth metal, or an ammonium compound;
an anodic protic-soluble electrochromic material of represented by Formula (III):

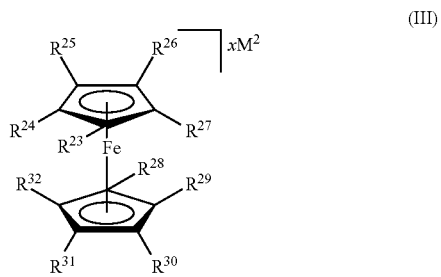

(III)

wherein
$R^{23}$ and $R^{28}$ are each independently alkyl or alkyl substituted with a carboxylate, phosphonate, phosphate, or sulfonate, provided that at least one is alkyl substituted with a carboxylate, phosphonate, phosphate, or sulfonate;
$R^{24}$, $R^{25}$, $R^{26}$, $R^{27}$, $R^{29}$, $R^{30}$, $R^{31}$, and $R^{32}$ are each independently H or alkyl;
x is an integer corresponding to the number of carboxylate, phosphonate, phosphate, sulfonate groups; and
$M^2$ is independently at each occurrence an alkali metal, an alkali earth metal, or an ammonium compound; and
an anodic protic-soluble electrochromic material represented by Formula (V), (VI), or (VII)

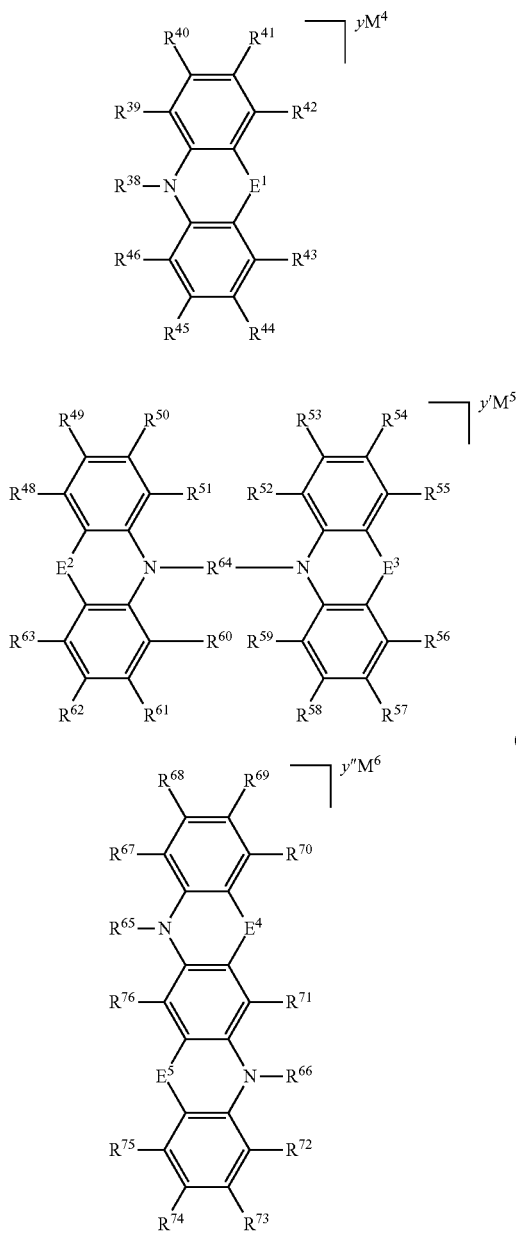

wherein
E¹, E², E³, E⁴, and E⁵ are each independently O, S, or NR⁴⁷;
R³⁸, R⁴⁷, R⁶⁵, and R⁶⁶ are independently at each occurrence an alkyl group substituted with a carboxylate, phosphonate, phosphate, or sulfonate;
R³⁹, R⁴⁰, R⁴¹, R⁴², R⁴³, R⁴⁴, R⁴⁵, R⁴⁶, R⁴⁸, R⁴⁹, R⁵⁰, R⁵¹, R⁵², R⁵³, R⁵⁴, R⁵⁵, R⁵⁶, R⁵⁷, R⁵⁸, R⁵⁹, R⁶⁰, R⁶¹, R⁶², R⁶³, R⁶⁷, R⁶⁸, R⁶⁹, R⁷⁰, R⁷¹, R⁷², R⁷³, R⁷⁴, R⁷⁵, and R⁷⁶ are each independently H, F, Cl, Br, I, CN, OH, O-alkyl, SH, S-alkyl, NO₂, alkyl, aryl, or amino, or any two adjacent groups of join to form a monocyclic, polycyclic, or heterocyclic group;
R⁶⁴ is alkylene;
y, y', and y" are each independently an integer corresponding to the number of carboxylate, phosphonate, phosphate, sulfonate groups; and $M^4$, $M^5$, and $M^6$ are independently at each occurrence an alkali metal, an alkali earth metal, or an ammonium compound.

2. The electrochromic medium of claim 1, wherein in Formula (II)
$R^{12}$ and $R^{21}$ are each independently —$(CH_2)_s$—$CO_2^-$, —$(CH_2)_t$—$P(O)(OH)(O^-)$, —$(CH_2)_u$—$OP(O)(OH)(O^-)$, or —$(CH_2)_w$—$S(O)_2O^-$; and
s, t, u, and w are each independently 1, 2, 3, 4, 5, 6, 7, 8, 9, or 10.

3. The electrochromic medium of claim 1, wherein in Formula (III)
$R^{23}$ and $R^{28}$ are each independently alkyl, —$(CH_2)_{m'}$—$CO_2^-$, —$(CH_2)_{n'}$—$P(O)(OH)(O^-)$, —$(CH_2)_{p'}$—$OP(O)(OH)(O^-)$, or —$(CH_2)_{q'}$—$S(O)_2O^-$; and
m', n', p', and q' are each independently 1, 2, 3, 4, 5, 6, 7, 8, 9, or 10.

4. The electrochromic medium of claim 1, wherein the cathodic protic-soluble electrochromic material of Formula (I) is

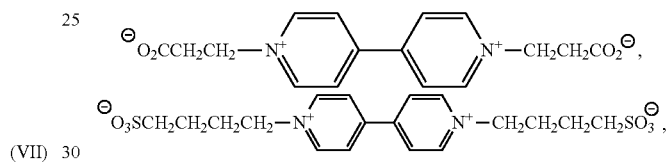

or a mixture thereof.

5. The electrochromic medium of claim 1, wherein the anodic protic-soluble electrochromic material of Formula (III) is

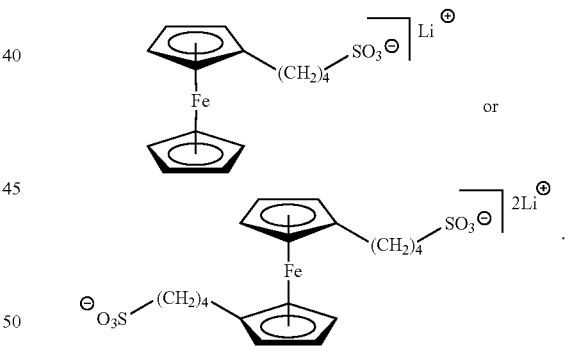

6. The electrochromic medium of claim 1, wherein the anodic protic-soluble electrochromic material of Formula (V) is

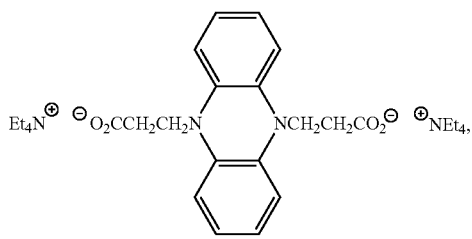

-continued

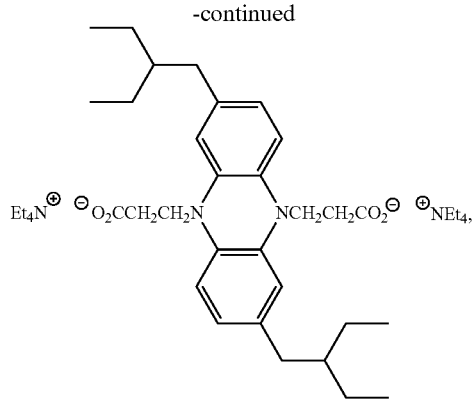

or a mixture thereof.

7. The electrochromic medium of claim 1, wherein the protic solvent comprises an alcohol, a carboxylic acid, a primary amino compound, a secondary amino compound, water, or a mixture of any two or more thereof.

8. The electrochromic medium of claim 1, wherein the protic solvent comprises methanol, ethanol, isopropanol, trifluoroethanol, butanol, ethylene glycol, propylene glycol, water, or a mixture of any two or more thereof.

9. The electrochromic medium of claim 1, wherein the protic solvent comprises a diol.

10. The electrochromic medium of claim 1, wherein the amount of protic solvent in the liquid or gel is from about 40 wt % to about 100 wt %.

* * * * *